US011554186B1

(12) United States Patent
Lai

(10) Patent No.: US 11,554,186 B1
(45) Date of Patent: Jan. 17, 2023

(54) AIRFLOW UV QUARANTINE METHOD AND AIRBORNE INFECTION UV QUARANTINE DEVICE

(71) Applicant: Yi Yu Lai, Brampton (CA)

(72) Inventor: Yi Yu Lai, Brampton (CA)

( * ) Notice: Subject to any disclaimer, the term of this patent is extended or adjusted under 35 U.S.C. 154(b) by 0 days.

(21) Appl. No.: 17/067,384

(22) Filed: Oct. 9, 2020

(51) Int. Cl.
*A61L 2/00* (2006.01)
*A61L 9/20* (2006.01)

(52) U.S. Cl.
CPC .............. *A61L 2/0047* (2013.01); *A61L 9/20* (2013.01); *A61L 2202/11* (2013.01)

(58) Field of Classification Search
CPC ....... A61L 9/20; A61L 2/0047; A61L 2202/11
See application file for complete search history.

(56) References Cited

U.S. PATENT DOCUMENTS

| 2006/0241729 | A1* | 10/2006 | Dawson | A61N 5/0624 607/94 |
| 2009/0272029 | A1* | 11/2009 | Aiking | A61L 2/10 47/1.43 |
| 2015/0367008 | A1* | 12/2015 | Romo | A61L 2/10 422/24 |

* cited by examiner

*Primary Examiner* — Sean E Conley
(74) *Attorney, Agent, or Firm* — Michael D. Eisenberg

(57) ABSTRACT

The systems and methods herein involve an infection ultraviolet (UV) device where an enclosed area is exposed to 254 nanometer (nm) radiation, thereby reducing and quarantining airborne pathogens and microbes. This reduces transfer of said pathogens and microbes among individuals equipped with UV protection in the enclosed area.

8 Claims, 8 Drawing Sheets

AIRFLOW UV QUARANTINE METHOD AND AIRBORNE INFECTION UV QUARANTINE DEVICE

TECHNICAL FIELD

This invention relates to UV quarantine systems applied for pandemic control, disease control, pest control, and industrial good manufacturing practices. The UV quarantine systems remove microbes and airborne contagious agents, thereby supporting an air inaccessible distancing code of practices for replacing social distancing protocols.

The SARS-CoV-2 (corona virus or COVID-19) is continuing to spread across the world, with more than 10 million confirmed cases in 212 countries and over 500,000 deaths worldwide as of June 2020. During the coronavirus crisis, immunological solutions have been suggested, which are limited to the range of acquired immunity (antigen-specific immunity). Little is known or capable of handling with innate immunity (non-specific immune protection). The success rate of a vaccine is inversely proportional to its required innate immunity. This requirement makes the effectiveness strongly based on age-dependence. Cancer is an extreme example of innate immunity as 100% innate immunity is required. This is attributed to not having an immunized external antigen. Therefore, reliance on only a vaccine against COVID-19 is methodologically inappropriate.

For other vaccine intentioned illnesses with decreasing requirements to innate immunity, certain demographics gradually adapt to the immunological solutions. Ideal targets for immunization should be problems that require: (i) less or zero innate immunity and (ii) a sensitive acquired immune response. Innate immunity is strongly age-related and results in immunosenescence. Thus, populations older than 65 years cannot be activated for immune protection by any immunological solutions. For the case of COVID-19, it is still unknown how much innate immunity and how much adaptive immune response sensitivity are required for a successful vaccine.

Additionally, the envelope of the COVID-19 virus possesses human cell membrane ingredients that detach from a host organism. Thus, the protein and ribonucleic acid (RNA) particle can be dealt with adaptive immunity. The envelope relies on innate immunity for counteracting infection, which needs further investigation to understand to develop a vaccine against COVID-19.

Further, a successful vaccine against COVID-19 is likely to make a substantial number of immunized individuals into asymptomatic coronavirus carriers. Asymptomatic coronavirus carriers are still capable of transmitting COVID-19 to other individuals. Complications from COVID-19 are not removed by a successful vaccine against COVID-19.

Due to technological difficulties in manipulating innate immunity in developing the vaccine against COVID-19, and the ineffectiveness of social distancing, enhanced quarantines are needed.

BRIEF SUMMARY OF EMBODIMENTS OF THE INVENTION

In a variant, a method for ultraviolet (UV) disinfection comprises: irradiating with UV light within an enclosed area with an infection UV quarantine device; shielding individuals within the enclosed area with UV shielding technology; reducing airflow accessibility of airborne pathogens and respiratory droplets within the enclosed area; reducing access of the individuals within the enclosed area to the airborne pathogens and the respiratory droplets by killing airborne pathogens and respiratory droplets within the enclosed area; measuring UV exposure levels of the individuals within the enclosed area by utilizing a UV meter; and wherein the infection UV quarantine device comprises a UV lamp and the UV shield comprises a radiation filter, wherein the radiation filters are composed of interchangeable parts.

In another variant, the UV lamp emits 240-280 nanometer radiation, wherein the radiation is germicidal to airborne pathogens and the respiratory droplets.

In yet another variant, the interchangeable parts are selected from the group consisting of: a UV radiation box, walls, and umbrellas.

In yet another variant, the radiation filter transmits visible light.

In yet another variant, the radiation filter blocks high-frequency light.

In yet another variant, the airborne pathogens are COVID-19, Newcastle disease, measles, morbillivirus, chickenpox, *Mycobacterium tuberculosis*, influenza, enterovirus, and norovirus.

In yet another variant, the respiratory droplets range from 5 micrometers and 1000 micrometers.

In yet another variant, 240-280 nanometer radiation travels up to 15 meters from the UV lamp.

In yet another variant, the infection UV quarantine device and the UV shield are applied in GMP environments, food treatment environments, and agricultural greenhouse pest control environment.

In yet another variant, shielding the individuals within the enclosed area with UV shielding technology comprises covering skin of the individuals within the enclosed area.

In yet another variant, fungi in regions under nails of a foot are treated with the infection UV quarantine device.

In yet another variant, the UV lamp emits 240-280 nanometer radiation for 30 minutes.

In a variant, an ultraviolet (UV) quarantine device comprises: a UV lamp configured to emit radiation for killing pathogens in an enclosed area; a UV shield configured to absorb high frequency radiation; and a containment box configured to receive the UV lamp.

In another variant, the enclosed area is a public area for containing one or more individuals, a private residence for containing one or more individuals, food processing plants, and a manufacturing site.

In yet another variant, the UV shield comprises a respirator box and tubes, wherein the tubes are operatively connected to the respirator box.

In yet another variant, the tubes are bent or chimney-shaped.

In yet another variant, wherein the pathogens are *E. coli*, COVID-19 droplets, and fungus.

In yet another variant, the UV lamp is an 8-watt variant, a 40-watt variant, and a 60-watt variant.

In yet another variant, an enclosed area is 8 square meters when the UV lamp is the 8-watt variant.

Other features and aspects of the invention will become apparent from the "UV partially shielding technology", taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
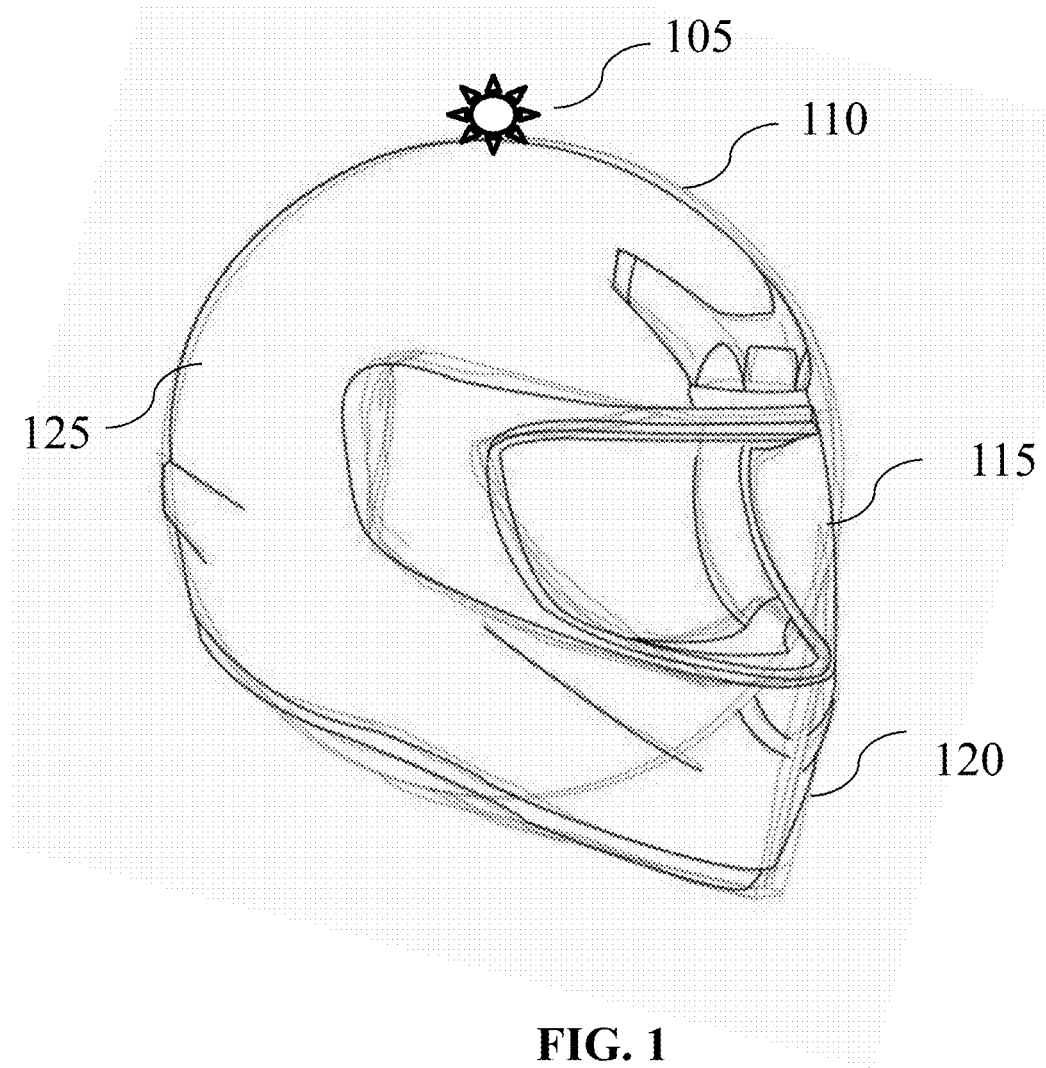
FIG. 1 is a depiction of a UV shield, in accordance with the principles of the invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Historically, the spread of and infection by contagious agents (i.e., pathogens) has been achieved by quarantining conventions. These quarantining conventions involve: masks, protective clothes, chemical sanitation, and quarantining hospitals. These quarantining conventions are associated with the following problems (P1, P2, P3, P4, P5, and P6).

P1: There is currently no efficient physical quarantine system to stop the COVID-19 infection. Conventional quarantine system, which include masks, protective cloth, chemical sanitation, and quarantining hospitals, are insufficient for stopping the spread of COVID-19.

P2: Social distancing rules are an inefficient way to stopping the spread of COVID-19, which is an airborne pathogen.

P3: The application of chemicals is a higher cost, lower efficiency solution to deal with airborne infection. The application of chemicals adversely impacts the environment.

P4: A vaccine is often perceived as the only way to stop the COVID-19 infection. However, vaccine development requires large investment of money and does not solve immunosenesence (i.e., the gradual deterioration of the immune system brought on by natural age advancement). Thereby, no matter which kind immunization technologies is used, sufficient immune protections are not activated for most people older than 65 years of age.

P5: Medicines for fungi foot (nails) are difficult to control and prone to relapsing (i.e., fungal infection returning).

P6: Good manufacturing practices (GMP) in food and pharmaceutical industries lack the application of UV disinfection. (UV radiation have been used widely in these two industries for certain processes. However, UV disinfections have never entered into the GMP standards.)

In contrast to quarantining conventions, the systems and methods herein provide the following quarantine environments (QE1, QE2, and QE3) via an infection ultraviolet (UV) quarantine device: (QE1) a partial or fully UV disinfected working environment within enclosed areas people on-site use; (QE2) UV protections for potentially exposed portions of human skin, thereby avoiding exposure to UV radiation; and (QE3) airflow inaccessible distancing. Aspects of the infection UV quarantine device involve: a UV radiation box, a UV radiation wall, and a UV hood. In some instances, the UV quarantine device may be constructed from some simple materials or purchased from commercial replacements. Thereby, QE1, QE2, and QE3 can be achieved conveniently at non-expensively.

QE1, QE2, and QE3 include the following technological aspects (TA1, TA2, TA3, TA4, TA5, and TA6).

TA1: Airflow inaccessible distancing protocols provide sustained quarantine and inoculation from microbes and airborne pathogens not observed with quarantine methods. During social distancing protocols, there is a 2 meter distance between individuals. Distancing alone is not a suitable factor to focus on for halting infection. Small aerosol particles can travel as far as 15 meters, or even 20-meters. Therefore, social distancing is ineffective at halting transmission of COVID-19, which can be a small aerosol particle or small droplet particle. Airflow inaccessible distancing is a protocol of the systems and methods herein which provides advantages over social distancing. Airflow inaccessible distancing is: (1) the disinfection of airflow, which can otherwise transport COVID-19 or other small aerosol particles and small droplet particles, by (2) the application of UV lamps and UV protection herein (e.g., UV hoods and UV radiation box (wall)); (3) the resulting elimination of all airborne pathogens in the airflow; and (4) the control of airflow. The control of airflow which halts airflow all together can be achieved by plastic films placed in an enclosed area shared by two or more individuals. A complete halt in airflow corresponds to zero chance of infection. However, a complete halt in airflow is difficult to obtain. Thus, enclosed areas in which airflow inaccessible distancing are applied (e.g., UV radiation spreading to 20 meters from the UV lamp) become airflow inaccessible places. Airflow inaccessible places are regions spanning 20 meters from the UV lamps that are 100% free of pathogens in the airflow.

TA2: UV disinfection technology kills and thereby eradicate microbes and airborne pathogens, such as COVID-19, within enclosed areas.

TA3: UV shield technology (e.g., UV hoods, UV radiation box, UV radiation wall, and umbrellas) is utilized by individuals in an enclosed area, thereby protecting the individuals in the enclosed area from exposure to the UV radiation. A radiation filter absorbs and dissipates UV radiation but allows visible light to be transmitted.

TA4: UVC 254 nm strength measuring instrument (e.g., UV meter only) evaluates the functional time of UV lamps and efficacy of the UV shield technology at protecting the individuals from harmful levels of UV exposure in the enclosed area.

TA5: Petri dishes are used for airborne microbial capture technology and evaluation of COVID-19 infection. *E. coli* has been used as an indicator for bio-contaminants for over a century. *E. coli* spray is used to simulate COVID-19 or other airborne microbes.

TA6: The application of photo radiation laser beam location is used for UV radiation boxes.

Quarantine Implementation Aspects (QIA) are applied within QE1, QE2, and QE3 to provide technical solutions which address P1, P2, P3, P4, P5, and P6.

QIA 1: UV disinfection has been applied for more than one century. However, people always operate the disinfection process while people are absent from a congregating region. In contrast, QIA 1 is implemented when (i) people are inside the congregating region and (ii) UV protection via UV shielding technology is used for public health requirements.

QIA 2: UV disinfection has been applied for more than one century. Diverse materials are used that allow visible lights through, while shielding off UV wavelengths. UV hoods for welders have also existed for decades, albeit in lower production. The systems and methods herein involve a combination of (1) UV hoods, (2) UV disinfection, and (3) materials which allow visible lights through and shield off UV light. The combination of 1, 2, and 3 disinfects the airborne contagious agents, thereby stopping airborne pathogens and microbial, especially COVID-19, from accumulating in the congregating region (e.g., a public area).

QIA 3: The materials of combination 3 provide convenient UV protection (i.e., a shielding effect) via the UV radiation box (wall), UV hood, etc., with various materials such as cardboard, clothes, wood, plastic, metal, umbrella, and any non-transparent materials. The shape of the UV protection can be varied to modify the shielding effect. UV hood can be expensive and cannot be readily self-made. Thus, the production of UV hoods is comparatively low and only used for welders. If there is increased use of UV hoods, shortages may result. As a precaution for the possible shortage, UV radiation boxes, UV radiation walls, and UV umbrellas are used in combination to provide the same level of safety from UV exposure, while killing airborne pathogens and microbes, such as COVID-19, Newcastle disease, measles, morbillivirus, chickenpox, *Mycobacterium tuberculosis*, influenza, enterovirus, and norovirus.

QIA 4: To evaluate the safety of these self-made or commercially purchased replacement products, a UV meter or similar (portable or non-portable) is used to test the safety of the shielded effect. Stated another way, the amount of UV radiation within the enclosed area and UV exposure levels to individuals in the enclosed area are measured by the UV meter.

QIA 5: The transmission mechanism of COVID-19 and other microbes are not well understood. Further, the transmission mechanisms among different contagious agents (airborne pathogens and microbes) may be variable. The transmission of COVID-19 is believed to be airborne by implementing a "airflow inaccessible distancing" protocol instead of a "social distancing" protocol. For example, a plastic film stops the airflow where the virus cannot penetrate the film of 1-millimeter (mm) thickness. However, airflow can transport COVID-19 viruses as to infect people as far as 15 meters (m) distance. Stated another way, airflow accessibility is 15 m and individuals can be infected within the 15 m. Therefore, the critical factor effecting the quarantine and inoculation of the virus is decreasing airflow accessibility and not increasing social distancing.

QIA 6: UV radiation is used for treating Athlete's Foot (Tinea Pedis) in combination with the UV partial shielding technology. The combination of the UV radiation and UV partial shielding technology exhibit advantages over chemical-based medicines (e.g., pharmaceutical agents).

QIA 7: UV radiation in combination with UV shielding technology is used in food or pharmaceutical industries for GMP regulations.

QIA 8: UV radiation in combination with UV shielding technology is used in agricultural greenhouse pest control.

QIA 9: Chemical sanitation for the inoculation of airborne viruses in enclosed areas, rooms, or hospitals used by a COVID-19 confirmed patient is infective. Thus, chemical sanitation is ineffective at fully cleansing enclosed areas (e.g., private rooms or hospitals) used by at least one COVID-19 confirmed patient for subsequent use by other individuals. Chemical sanitation which has some effectiveness for hard surfaces, is completely ineffective for small-sized aerosol particles within airflows within inside environments. High percentages of global COVID-19 casualties result from the incorrect use of chemical sanitation, whereby residual microbes and pathogens of infectious materials deriving from airborne viruses still persist. UV radiation kills the microbes and residual pathogens of infectious materials deriving from airborne viruses present on enclosed areas (e.g., private rooms or hospitals) used by at least one COVID-19 confirmed patient. Thus, the UV radiation of the systems and methods herein makes the enclosed areas (e.g., private rooms or hospitals) used by at least one COVID-19 confirmed patient suitable for subsequent use without spreading COVID-19. Stated another way, the residual microbes and pathogens of infectious materials deriving from airborne viruses are no longer persisting in surfaces or the air.

When using the infection UV quarantine device, protocols can be applied for an air inaccessible distancing, in which airborne pathogens are killed.

When using the infection UV quarantine device, UV radiation is impinging and irradiating utensils, equipment, or spaces, etc. for 30 minutes.

When using the infection UV quarantine device is used in private areas for family or public areas, then UV radiation boxes (walls) are used and placed in between individuals if than one individual is present in an enclosed area.

When using the infection UV quarantine device in enclosed areas that are severely infected regions or frequently visited areas, UV hoods may be used with the UV radiation boxes (or UV radiation walls).

The infection UV quarantine device is validated as being safe and cost effective for public usage, as investigated on DH5-alpha (a) strain of *Escherichia coli* (*E. coli*). Thereby, the infection UV quarantine device prevents the spread of all infectious agents, including COVID-19, in enclosed areas by UV radiation selectively quarantining, inoculating, and/or killing infectious agents without exposing human skin.

The infection UV quarantine device provides QE1, QE2, and QE3, which applies UV radiation for curing foot fungus or fungi underneath nails. This provides sustained therapeutic benefit in curing fungi over traditional chemical treatments or pharmaceutical agents. UV radiation of the infection UV quarantine device can selectively contact the fungus with fungi killing wavelengths, without adversely impacting the health of the human skin.

The infection UV quarantine device provides QE1-QE3 which can be used for: (i) killing pathogens in food manufacturing and agricultural greenhouses; and (ii) killing higher order organisms, such as insects, or scaring off vermin, thereby achieving pest control.

Technical solutions of the systems and methods herein to technical problems, as described above, provide airflow inaccessible distancing.

The UV hood of the systems and methods herein, as depicted in FIG. 1, comprises UV shield 115, mouth piece 120, lamp mount 110 configured for receiving UV lamp 105, and interface 125 which connects mouth piece 120 to lamp mount 110. While UV lamp 105 emits 254 nm radiation from any angle, UV shield 115 is able to: (i) transmit visible light through; absorb UV radiation; and reduce optical process which adversely impact an individual's eye by diffusing reflection, refraction, semi-transmission, and transmission of high frequency light. The UV hood can offer 100% safety for individuals to use under QE1, QE2, and QE3. Mouth piece 120, interface 125, and lamp mount 110 protect skin extending from the head to the neck of the individual wearing the UV hood. Within mouth piece 120 and interface 125, respiratory boxes with vent holes are operatively connected to chimney/bent tube extenders, thereby preventing UV radiation leaking, such as box 210.

Figure 2:
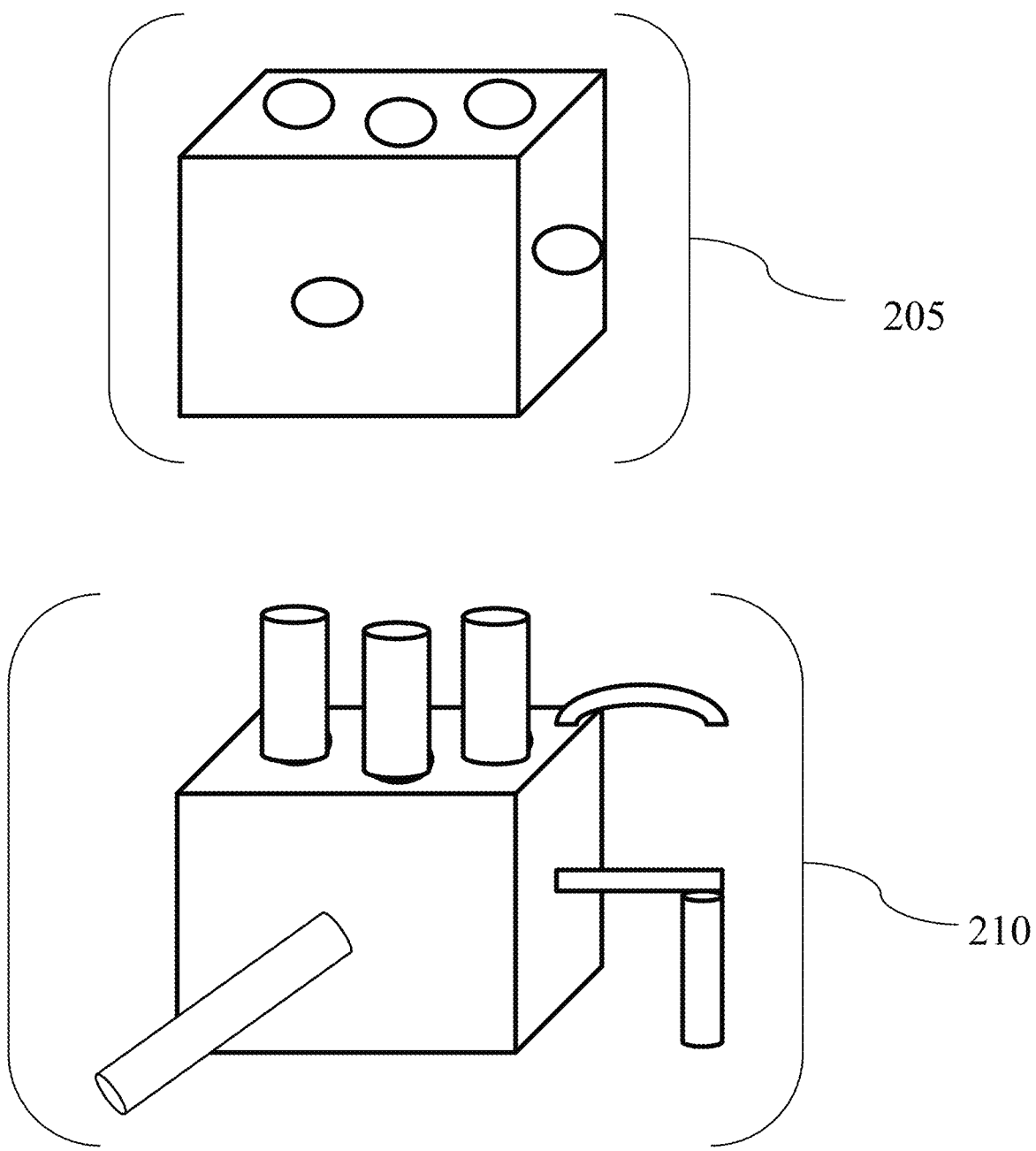
FIG. 2 is a depiction of a respirator box, in accordance with the principles of the invention.

As depicted in FIG. 2, respiratory boxes with vent holes on a solid surface not operatively connected to the chimney/bent tube extenders, such as box 205, are prone to leak UV radiation into the UV hoods. In contrast to box 205, box 210 is equipped with vent holes on a solid surface with the chimney/bent tube extenders prevent UV radiation from leaking in the UV hood from any angle.

Figure 3:
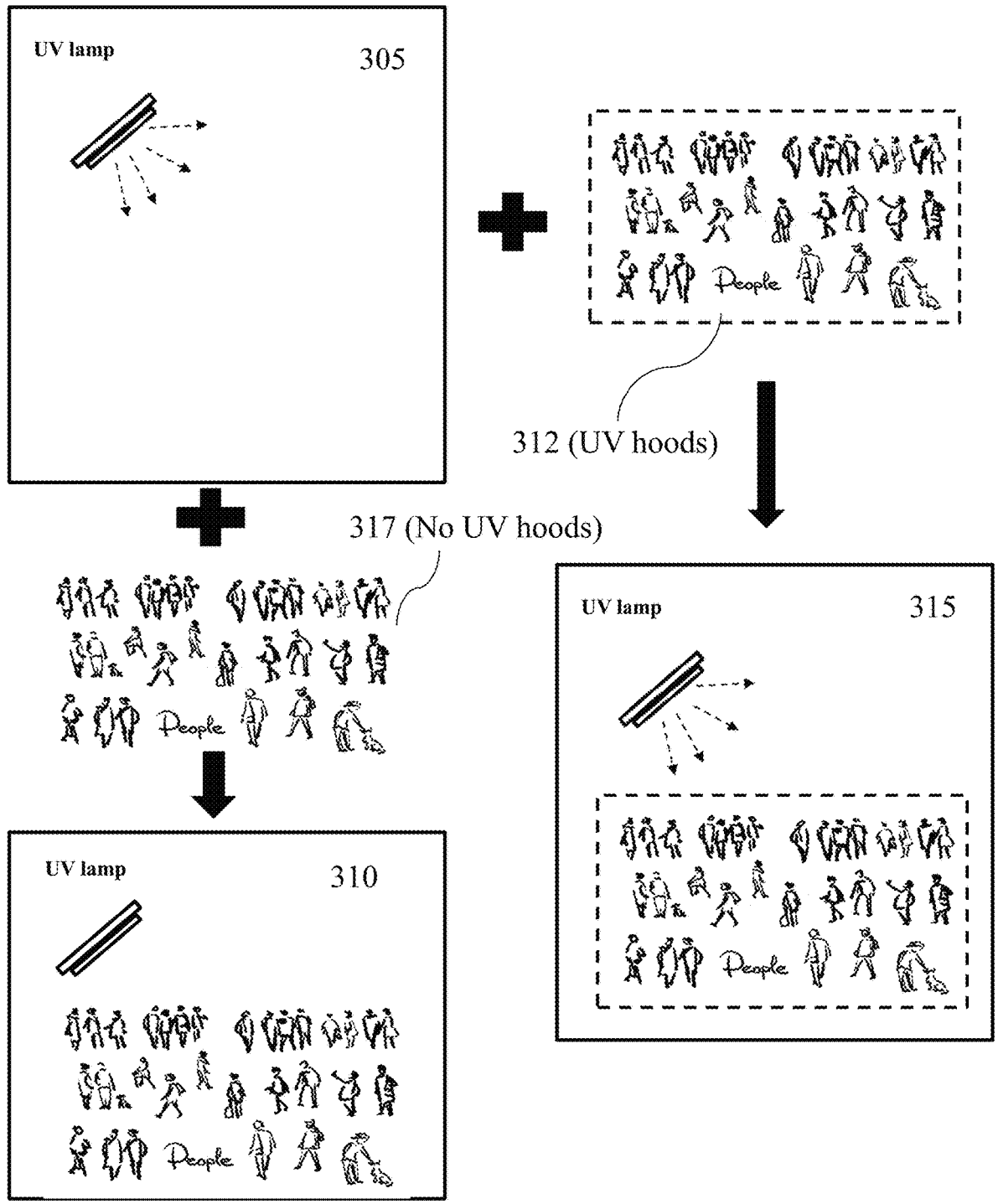
FIG. 3 is a depiction of the difference between the conventional UV disinfection and the quarantine infection environments provided by the UV disinfection, in accordance with the principles of the invention.

As depicted in FIG. 3, the UV lamp, and UV shielding (e.g., UV hood) support QE1, QE2, and QE3. A UV lamp is emitting UV radiation, thereby irradiating environment 305 and killing microbes and airborne pathogens therein. Conventional UV radiation disinfection processes (no UV hood) do not allow group of people 117 to go on-site as human skin or eyes are exposed to UV radiation. In turn, the UV lamp cannot be operated as depicted in environment 310. Thereby, microbes and airborne pathogens are not killed and disinfection is not being achieved. In contrast to conventional radiation disinfection processes, group of people 112 is equipped with UV hoods, thereby: (i) protecting human skins or eyes from UV radiation exposure and (ii) allowing people on-site in environment 315, while UV lamp is emitting UV radiation, thereby irradiating environment 315 and killing microbes and airborne pathogens therein. Environment 315 corresponds to a protocol for infection control in enclosed areas, such as stores and physical locations for conducting business (e.g., office spaces and factories) which are located in public areas and private residences.

Figure 4:
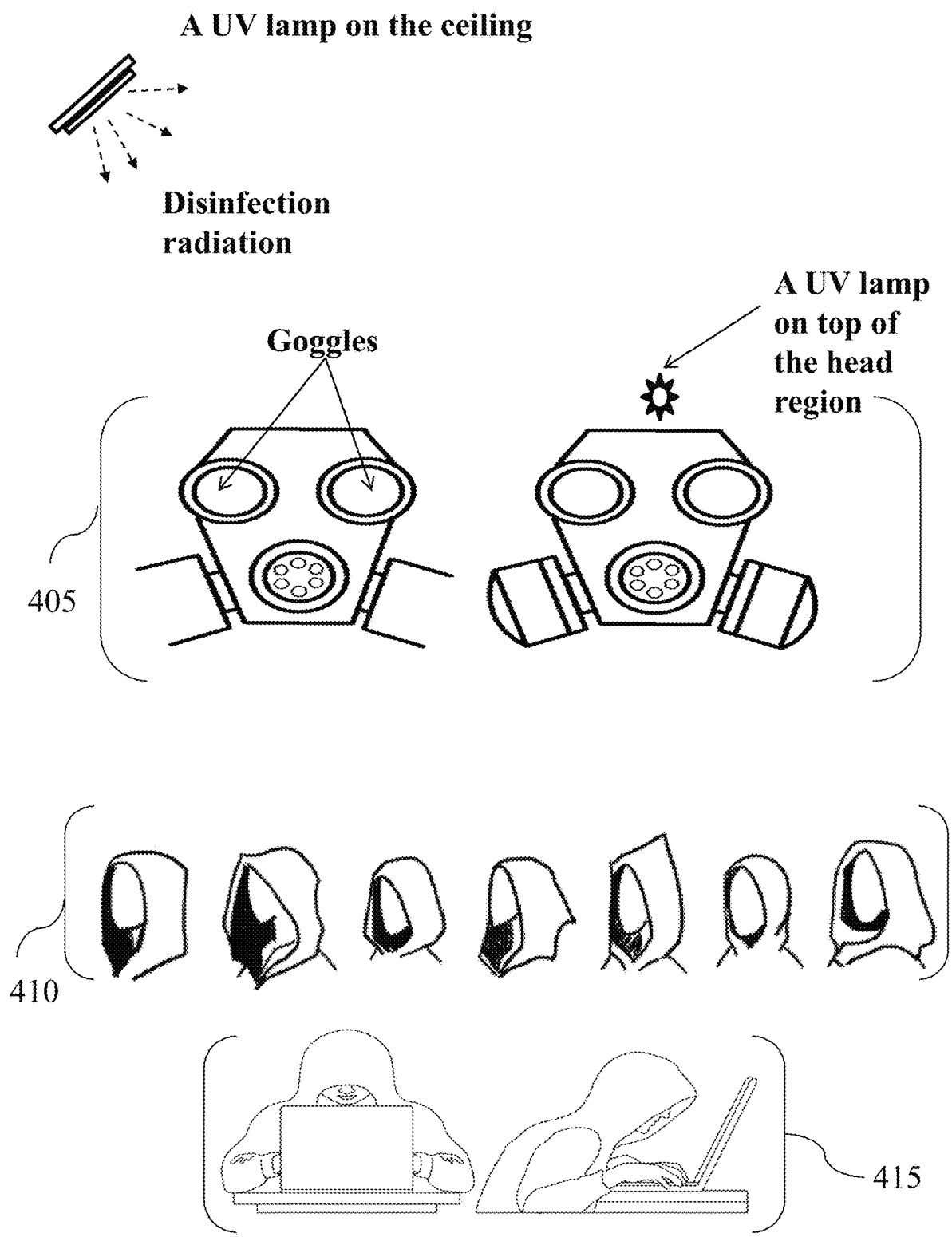
FIG. 4 is a depiction of UV masks and UV hoods, in accordance with the principles of the invention.

As depicted in FIG. 4, an individual wearing UV hood 405 can be equipped with an attached UV lamp (right) or without the UV lamp (left). UV hood 405 can be used in an environment where the UV lamp on the ceiling emits disinfection radiation. The goggles absorb UV radiation and transit visible light, thereby protecting the eyes from UV radiation and not obscuring vision of the individual wearing UV hood 405. UV hood 405 contains a mouthpiece (with six breathing holes) and left and right breathing cartridges, which provide and release purified and disinfected air, for consumption by individuals wearing UV hood 405. UV hood 405 provides complete protection for the head and mouth regions of the individual wearing UV hood 405 from UV radiation and pathogens. UV hood 405 is composed of heat and UV dissipating materials, such that the absorbed UV radiation does not accumulate as prevent increases in temperatures of UV hood 405. This guards against discomfort for individuals wearing UV hood 405.

As depicted in FIG. 4, UV hood 410 covers the head and neck, while exposing the face. UV hood 410 is composed of materials which can: (i) absorb UV radiation and (ii) be used in setup 415 where individuals can be present nearby each other without a mask covering the mouth region. Stated another way, UV hood 410 in setup 415 allows individuals to be close to each other in QIE1, QIE2, and QIE3. In setup 415, the two individuals, each wearing UV hood 110, are facing directions as to be perpendicular to each other. Wearable accessories can be used on other parts of the body which can be exposed to UV radiation.

Figure 6:
FIG. 6 is a depiction of UV umbrellas, in accordance with the principles of the invention.

As depicted FIG. 6. alternative UV protection systems to UV hoods can be used. The alternative UV protection systems to the UV hoods 405 and 410. Dark-colored umbrellas in FIG. 6 can provide temporary protection from exposure from UV radiation.

Figure 5:
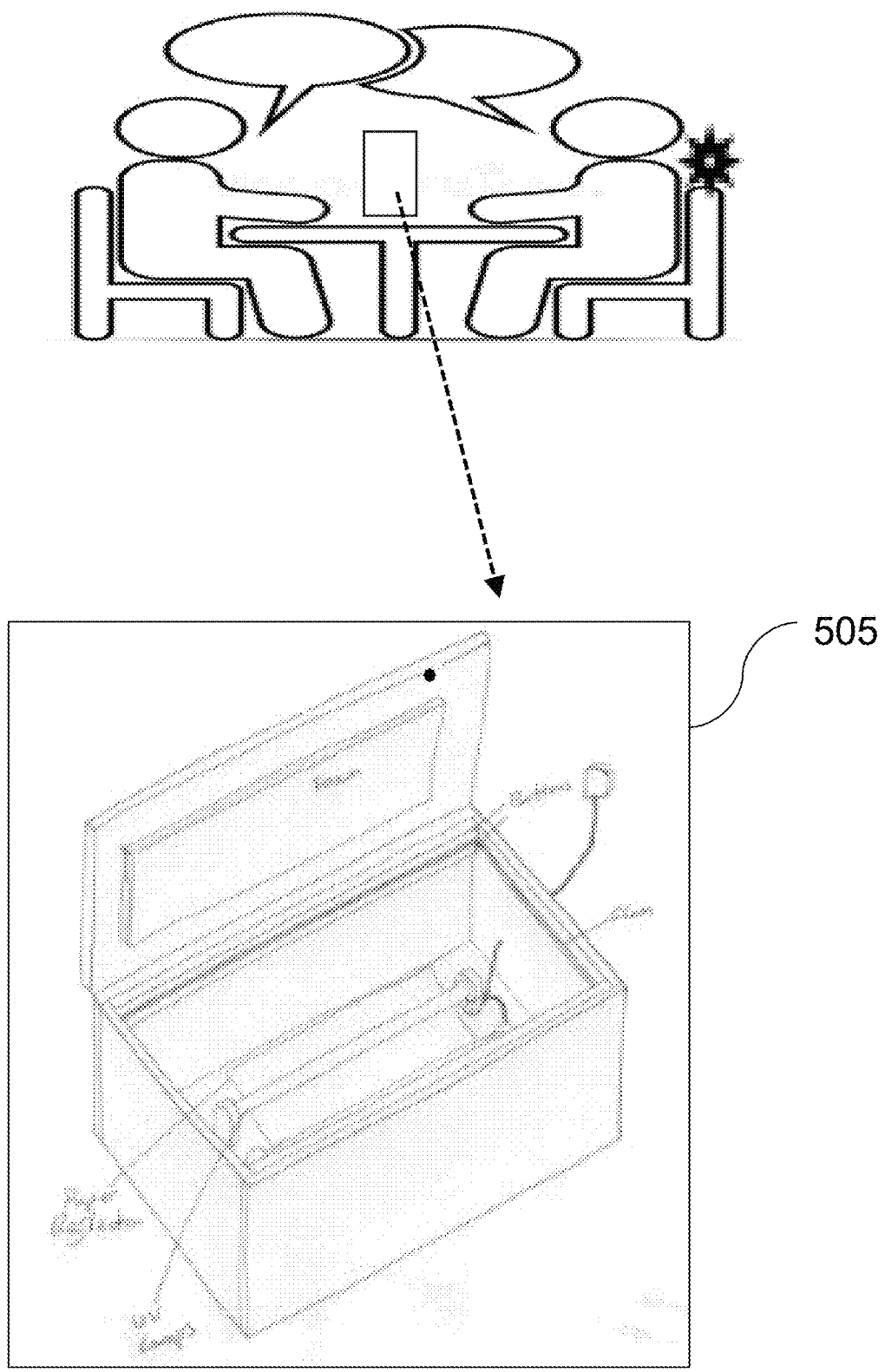
FIG. 5 is a depiction of a UV radiation box, in accordance with the principles of the invention.

UV hoods 405 and 410 are composed of compensation materials (i.e., a 'counter-procedure' plan on expected side effects) which: (i) allows visible lights through and (ii) absorbs and shields UV radiation. The production of the compensation materials is lower than other types of materials so shortages are possible. To counter this, the compensation materials are replaceable and interchangeable in case there are shortages in materials for constructing the UV hood in FIG. 1, UV hood 405, and UV hood 410. Additionally, UV radiation box 505 (wall) can be used for such compensation applications, which kill microbes and airborne pathogens. Within UV radiation box 505 depicted in FIG. 5, paper covering 515 is underneath lamp 520. In the opened state of UV radiation box 505, foam 515, buttons 510, and seal 525 are viewable and lamp 520 emits radiation. UV radiation box 505 can be used in setup 503 where the individuals are not wearing masks and are facing each other. The box and the arrangement of lamp 520 are able to emit radiation which kills airborne pathogens, while absorbs UV radiation approaching the individuals in setup 503. Thereby, setup 503 achieves QIE1, QIE2, and QIE3 for individuals within enclosed areas.

To validate the safety of self-made or commercially purchased UV protection, a portable UV meter or similar device is used. As indicated above, UV levels in the enclosed areas and the amount of UV light impinging an individual are measured. In combination of the UV meter with the above, the quarantine of the systems and methods here exhibit: (i) facile implementation in publicly enclosed areas;

(ii) high anti-infection efficiency (i.e., disinfecting a contaminated area within 30 minutes); and (iii) maintaining disinfection within the enclosed area.

Technical advantages of the airflow inaccessible distancing include a quarantining effect (i.e., isolating pathogens) and an inoculating effect (i.e., reducing properties leading to infection) against: (i) small sized aerosol and droplet particles implicated in the spread of infection; and (ii) populations of particles implicated in the spread of infection, which are stabilized in the airflow. The size of small sized aerosol particle is <10 µm. The size of droplets is >10 µm. Further, the quarantining effect and the inoculating effect can be applied against liquid particles, solid ingredients, sticky materials, and complex biological systems (e.g. human saliva). Human saliva includes hundreds of bioactive ingredients, such as viral RNA, DNA, envelop S proteins, antibodies, etc. The airflow inaccessible distancing, as provided by the systems and methods herein, create a capturing environment for investigating small aerosols and small droplets for medical studies. This is contrast to other capturing environments, which are suited for large aerosols and large droplets.

Technical advantages of the airflow inaccessible distancing include a quarantining effect (i.e., isolating pathogens) and an inoculating effect (i.e., reducing properties leading to infection) against aerosol particles generated by human engaging in speaking and normal breathing. The aerosol particles generated by humans engaging in speaking and normal breaking range from 0.75 µm to 1.1 µm. This is smaller than aerosol particles generated by humans coughing or sneezing, which are 5 µm. Therefore, small aerosol particles, small droplets, and aerosol particles generated by humans engaging in speaking and normal breathing are expected to persist longer in airflow and be transmitted further distances than larger particles. Validating experiments are shown in Table 3, where *E. coli* spray viable colony counting increases to ten folds as in and UV radiation of the systems and methods herein kill these bacteria.

Technical advantages of the airflow inaccessible distancing include killing airborne microbes including COVID-19 viruses in the airflow of public areas within the time scale of seconds, which correspond to human speaking, normal breathing, coughing, or sneezing. Validating experiments are shown in Table 3 and Table 4.

Technical advantages of the airflow inaccessible distancing include bolstering or supplanting chemical sanitation, which is widely used everywhere. Chemical sanitation is insufficient for aerosol disinfection due to mixing efficiency and decaying processes due to surface tension. The small size of the aerosols or liquid particles imparts challenges for efficient mixing, as performed during chemical sanitation. Chemical sanitation, for killing the COVID-19 viruses inside small-sized liquid particles, is therefore ineffective, inefficient, or both ineffective and inefficient. In contrast, UV radiation of the systems and methods herein are able to effectively contact the small aerosol particles or small liquid particles containing COVID-19 viruses within. The UV radiation disrupts the structure of the small aerosol particles or small liquid particles. The protein sheath (or envelope) of COVID-19 is initially weakened and subsequently breaks down by the UV radiation. This exposes the rest of the COVID-19 structure to the UV radiation, thereby denaturing the amino acid sequence (arranged in tertiary and quaternary structures) by disrupting hydrogen bonding motifs and initiating free-radical processes involving hydrogen atom abstraction. Thus, chemical sanitation is not as efficient as UV radiation of the systems and methods herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

EXAMPLES

Airflow inaccessible distancing, as experimentally validated by the infection UV quarantine device applied on *E. coli* DH5a spray viable colony counting simulation, is a safety upgrade over social distancing. In contrast to quarantining contagious agents via masks, protective clothes, chemical sanitation, and quarantine hospitals composed of system elements, the infection UV quarantine device for airflow inaccessible distancing creates a partial or fully UV disinfecting working environment within an enclosed area. The infection UV quarantine device and accompanying UV protections within the enclosed area may include: (1) a UV radiation box; (2) a UV radiation wall equipped with a UV lamp; and (3) a UV hood. To protect against UV radiation, individuals within the enclosed area utilize the UV protections to prevent radiation from impinging exposed skin of the individuals within the enclosed area.

Procedures which use the infection UV quarantine device and the accompanying UV protections include: (i) 30 min UV disinfection for utensils, equipment, or spaces, etc., in enclosed areas (e.g., private area in use by families or public regions); and (ii) turn the UV radiation boxes (walls) on if more than one individual need to share them. In severely infected regions or high frequency visited areas, UV hoods of the systems and methods herein can replace the UV radiation boxes (walls) of the systems and methods herein for sufficient disinfection.

The enclosed area in which the UV lamps and UV hoods are used may be large public regions, such as supermarkets, libraries, large playing grounds, airports, cinemas, etc. These large public regions generally only allow a small number of alternative UV protections. For the best results, individuals within the enclosed area use the UV hood of the systems and methods herein.

STEP 1: Install or check the installed UV lamps in the enclosed area (i.e., a space or public region). In a room, a public region, or a family region, based on the manufacturer's instructions, evaluate how many UV lamps are required, how to distribute UV lamps, and whether remote controls are suitable for the enclosed area. Generally, an 8 W UV disinfection lamp can emit radiation as to irradiate an 8 m$^2$ space, including all of the utensils and equipment therein. Sometimes on-site measurements are necessary. UV lamps that can be used are: (i) 8 watt (W) UV lamp without remote control, lamp and accessory (81 grams) and 1.5 m line and switch (115 g); (ii) 40 W UV lamp without remote control, lamp and accessory (268 g) and 1.5 m line and switch (135 g); (iii) 40 W double UV lamp with remote control and metal protect (541 g); and (iv) 60 W UV lamp without remote control, lamp and accessory (372 g) and 1.5 m line and switch (135 g).

STEP 2: Check the functional life of all UV lamps. If the radiation of a UV lamp is below 70% of the designed strength, then a replacement UV lamp is needed. For example, photo radiation laser location technology can be used to determine if the UV lamp needs to be changed. The photo radiation laser location technology is for testing the mobility safety of UV radiation box, UV umbrella, etc. The laser locator has a locating distance ranging from 5-20 meters. This is widely used in industrial processes. There are instances of UV radiation box moving. The movements can correspond to angles which are not safe. The laser locator can predict and assess the angles that are not safe. In a public region, there are many UV lamps. Some of the angles may be not be safe for an umbrella. The laser locator detects these unsafe angles for the umbrella. The umbrella is only used under urgent conditions of people lacking a UV hood. In contrast, the UV hood is safe at any angle.

STEP 3: Implement UV 30 min protocol for infection less severe region or UV ultimate method for infection severe region. For the UV 30 min protocol for reducing infection in less severe regions, 30 UV radiation for the region are configure and arranged twice daily, while individuals are not on-site. For the UV ultimate method for reducing infection in more severe regions, all UV lamps of switched on. After 30 min, individuals are allowed to enter the region with a proper UV hood. For those who fail to bring their own UV hoods, a UV protection umbrella can be used.

Example 1—Reviewing Conventional Quarantining Systems

To experimentally validate the infection UV quarantine device, critical control points of the conventional quarantine system—masks, helmet, and protective clothes—are assessed. These critical points impose obstacles in providing effective quarantine environments. As depicted in FIG. 7A, the area denoted with the dotted line can be defined as "naked skin contact margin". The critical point which corresponds to the naked skin contact margin are regions of potential exposure to airborne pathogens. As depicted in FIG. 7B, regions of exposure can be found in the helmet designs, as denoted by the dotted lines. Particle sizes of viruses are smaller than particle sizes of bacteria, and cannot be: (i) "filtered" by bacterial filters designed for particle sizes not less than 0.2 μm and (ii) subsequent vacuuming steps. Further, bacteria or viruses in aerosol or droplet form cannot be separated from an airflow via filtering mechanisms. As depicted in FIG. 7C, advanced gas masks have to rely on two prerequisite designs that are critical points which impose obstacles in providing effective quarantine environments. These two prerequisite designs are: (i) arrangement of features avoiding the virus invading from the naked skin contact margin; and (ii) an active carbon cylinder or similar device for the absorption of the viruses. Stated another way, an absorption process instead of a filter can satisfy human respiration volume requirements, while removing the pathogens from an airflow. For those types of designs, active carbon cylinders must be renewed in a certain period after saturated. There is currently no existing technology which is practical in replacing active carbon devices. The critical control points in FIGS. 7A, 7B, and 7C can be attributed to insufficiency in stopping aerosol infection. Protective clothes must connect with advanced gas masks to avoid naked skin contact margin leaking. Otherwise, the advanced gas masks easily lose their protective functions.

Example 2—Validation of UV Disinfection

Airflow inaccessible distancing, as experimentally validated by the infection UV quarantine device applied on *E. coli* DH5a spray viable colony counting simulation, is a safety upgrade over social distancing.

While global attention focus on COVID-19 immunological solution, vaccines may compromise immunosenescence and leave people older than 65 years of age inactive to any immobilization. Additionally, social distancing provides fleeting effectiveness in quarantining the spread of airborne droplets. The infection UV quarantine device involves irradiating UV radiation in an enclosed area used in combination with UV hoods. UV radiation contacts and thereby kills the airborne pathogens and other pathogens residing on solid or liquid surfaces. UV radiation, which is continuously emitted in the enclosed area, is also shielded from individuals wearing/using the UV hood. Segregation of contagious airborne pathogens in this airflow inaccessible distancing environment is thereby achieved, as validated in $10^6$ cell/ml of *E. coli* DH5a spray viable colony simulation in a static room. As further indicated by the examples below, the airflow inaccessible distancing environment code reduces the spread of the contagious microbes and airborne pathogens. The infection UV quarantine device is further validated by spraying methods. Portable UV 254 nm or Geiger counters can measure UV radiation levels in the enclosed area to further ensure that UV radiation levels are safe.

Example 3—Disinfection of Aerosol and Droplet Particles

UV disinfection is used in a variety of applications, such as food, air, and water purification. According to current evidence, the COVID-19 virus is primarily transmitted between people through respiratory aerosols (<10 μm), droplets (>10 μm), and contact routes. Airborne droplets can persist in the air for several minutes. Smaller aerosols do not rapidly settle and can persist for longer durations to hours. The COVID-19 virus has been found to remain viable (i.e., actively contagious) as aerosol particles for 3 hours. The COVID-19 virus is more stable as droplet particles on plastic and stainless steel, copper, cardboard, and glass. The duration of detection of COVID-19 on metal, cardboard, and glass surfaces are up to 72, 4, 24, and 84 h, respectively. The social distancing rule of 2 meters is therefore insufficient. Ventilation airflow complicates the infection routes. The transparent properties of droplets and aerosol make UV radiation, as provided by the systems and methods herein, effective for contacting airborne COVID-19 aerosols and droplets particles and thereby disinfecting of enclosed areas.

Example 4—UV Radiation Preferred Over Chemical Sanitation

The infection UV quarantine device of the systems and methods herein obviate the need chemical sanitation for airborne microbes. The prerequisite condition for chemical sanitation is the mixture rate. If the airborne coronaviruses reside inside aerosols smaller than 1 μm, then chemical sanitation may be suitable. Solution of chemical sanitizing agents must be able to effectively mix or be in contact with <1 μm aerosol particles. In actual environmental conditions, there exists complex electrostatic repulsions and surface tension among airborne liquid particles which are <1 μm. The airborne liquid particles less than <1 μm can reside in the air for months and still not condense or precipitate.

Figure 8:
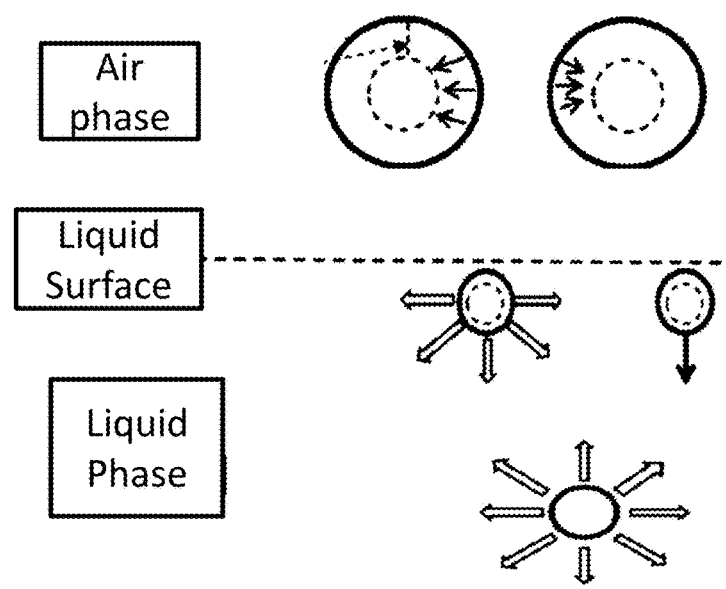
FIG. 8 is a depiction of surface tension region in aerosol and droplet particles, in accordance with the principles of the invention.

As depicted in FIG. 8, the surface tensions are denoted as dotted circles. Oscillation of the surface tension region (in the upper left particle) controls the stability of the air phase (i.e., aerosol particle). Smaller aerosol particles are stable in the airflow unless the smaller aerosol particles are in contact with an entity with a large specific area, such as human alveoli. When in contact with human alveoli, the smaller aerosol particles diffuse rapidly into the human alveoli. Petri dishes provide a suitable surface for capturing smaller aerosol particles. Thereby, there can be competitive binding between the agar of the petri dishes and the human alveoli surfaces. Two droplets (in the upper right particle) contact and combine with each other in the air, whereby surface tension forces stabilize the two droplets but makes it difficult to form larger mixed droplets. The center right particle is a liquid surface molecule which balances into inward facing forces, whereby surface tension forces establish dynamic thickness. The lower left particle is an inner liquid phase molecule or particle sending or releasing balanced forces, whereby there is no surface tension (as indicated by the absence of a dotted circle).

The smaller the aerosol particle size imparts increased difficulty in mixing and contacting with a solution of chemical sanitizing agents under equivalent conditions, based on specific surface area ratios, surface tension, and electrostatic repulsion. The size of aerosol particles generated by speaking and normal breathing is similar to each other, ranging from 0.75 to 1.1-μm. The size of aerosol particles generated by speaking and normal breathing are substantially smaller than the size of aerosol particles generated coughing or sneezing, i.e., ~5 μm. This means the aerosol particles generated by speaking and normal breathing can stay longer, reach further distances, and spread faster in the air than the aerosol particles generated by coughing or sneezing. These factors further make chemical sanitation effective at disinfecting the enclosed area from COVID-19.

Individuals are able to see macroscopic particles, such as chemical sprays applied in the enclosed area. COVID-19 aerosol particles are microscopic particles, thereby the chemical spray does not effectively mix with the COVID-19 aerosol particles. Surface tension may lead to a higher propensity for "elastic collision", which precludes mixing between COVID-19 aerosol particles and the chemical spray. After the chemical spray dissipates in the enclosed area and when individuals begin to use the enclosed area, the viruses inside the small aerosol particles emerge again. A high percentage of global COVID-19 casualties can be attributed to reliance on chemical sanitation for airborne viruses or a room which have been visited or heavily used by infected people. Stated another way, chemical sanitation is suitable for hard surfaces and unsuitable for small aerosol disinfection purposes. Hospitals largely rely on chemical sanitation to disinfect enclosed regions containing COVID-19. Therefore, hospitals inevitably become the secondary sources of infection or viral assembly site instead of a place capable of removing the virus by virtue of chemical sanitation being ineffective at killing aerosol particles. Contrary to chemical solutions, UV radiation is able effectively contact smaller size viral aerosol and droplet particles and subsequently kill the contacted smaller size viral aerosol and droplet particles. In Petri dish experiments, UVC can eradicate bacteria in seconds.

TABLE 1

Direct UVC Exposure Time Required to Achieve Eradication (0% growth)

| Organism | UVC exposure duration (seconds) |
|---|---|
| Methicillin-susceptible Staphylococcus aureus (MSSA) | 15 |
| Methicillin-resistant Staphylococcus aureus (MRSA) | 10 |
| Methicillin-susceptible, coagulase-negative Staphylococcus (MSCONS) | 10 |
| Methicillin-resistant, coagulase negative Staphylococcus (MRCONS) | 5 |
| Streptococcus pyogenes | 5 |
| Enterococcus species | 15 |

For airborne status, there is no clear data for the UVC bacterial disinfection since people never realize that there are significant differences between the germicidal curves on a hard surface and inside airflow for chemical sanitation, and the difficulty in the sampling of small-sized aerosols for physical parameter assay. For COVID-19, the eradiation time is significantly less than those of bacteria under an airborne state. This makes UV radiation substantially more effective at killing airborne microbes. Due to the difficulty of culturing and the risk of handling coronavirus specimens, *E. coli* DH5a suspension sprays simulate the coronavirus transmission. This low-risk species is used as a bio contaminant indicator for food, water, and air. The industrial standard is calibrated on notion that: (i) the increase of *E. coli* quantity in a sample is ascribed to the increase of certain targeted bio contaminant(s); and (ii) the decrease of *E. coli* in the sample is ascribed to the decrease of the targeted bio contaminant (s). Viable *E. coli* colony counting is therefore used to calibrate the aerosol contagious COVID-19 viral concentration to follow this canonical standard. Such a simulation is reliable as the guidance for stopping in vitro COVID-19 infection. The results of the simulation are equivalent to those acquired from other methods, thereby reliably validating "airflow inaccessible distancing" protocol.

Example 5—Validation of the 30-Minute UV Radiation Pre-Disinfection Protocol for Airborne Microbes The 30-minute UV radiation pre-disinfection protocol is applied for enclosed regions (e.g., public areas of use and family rooms originated from biosafety cabinet) and industrial cleanroom protocol which have been applied in research labs and pharmaceutical manufacturing. The 30-minute UV radiation pre-disinfection protocol in public areas of usage leads to virus eradication, whether the public area is used by symptomatic or asymptomatic coronavirus carriers. The drawbacks of chemical sanitation for small-sized viral aerosol particles due to the mixture efficiency can be overcome by the application of UV radiation in enclosed areas. Additionally, the application of UV in enclosed areas is a facile technique for implementation.

For a typical enclosed area, such as a room in use by a family, a 1-meter height center, a 2-meter, and a 3-meter circle on the same height plane are placed in a middle point of the room in the use by the family. On each circle, evenly distributed 5 sampling points are chosen. All of these sampling points are on a platform 1 m height from the ground and 1.5 m lower from the 40 W UV lamps in the middle. All the sampling points need to be away from the ground, ceiling, wall, door, window, ventilation inlets or outlets, etc. by at least 1 meter. Above 1-meter perpendicular of each sampling point, there is an 8 W UV lamp, such that there is a total of 10 sets of 8 W UV lamps on 10 sampling points. In all the experiments, the ventilation system is shut off. The operator uses sterilized protective cloth, hairnet, gloves, and shoe covers, while avoiding extra air turbulence.

Figure 7:
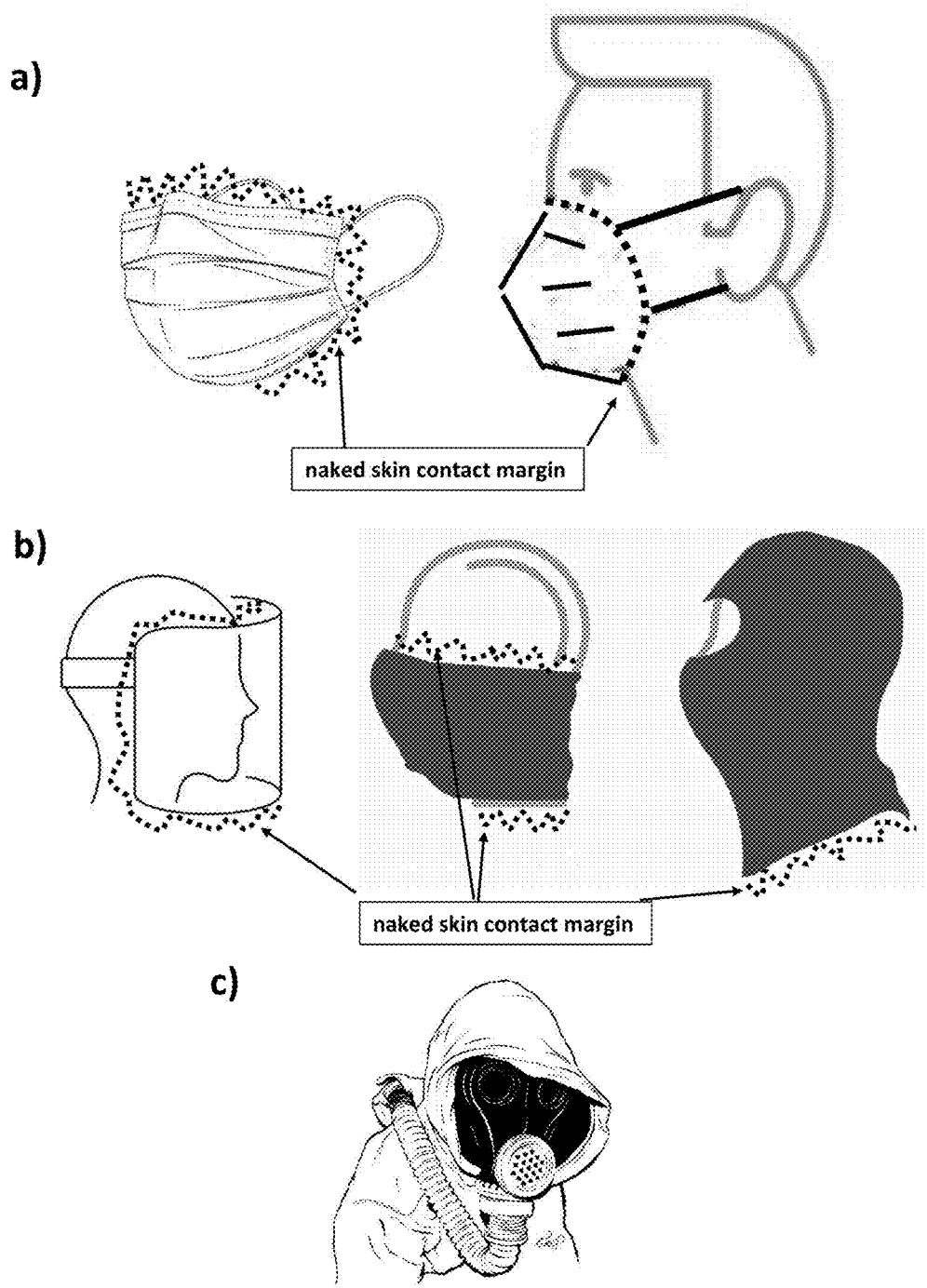
FIG. 7 is a depiction of face coverings, in accordance with the principles of the invention.

Within 1 hour after 30 minutes of UV radiation, the sealed plates are prepared with LB (Luria-Bertani) agar on each point as depicted in FIG. 7. The sealed plates are: (i) exposed for 5 min and 15 min duration at different times of 20 minutes, 40 minutes, and 60 minutes after the endpoint of the protocol; (ii) incubated at 37° C. for 48 hours; and (iii) checked for colony counting with 5-10 times magnifying glass. (If two or more overlapped colonies can be discerned, then count as the discerned colony number.) CKs (group without application of UV radiation) has not used any UV lamps in a week and start from the same time point (such as 10-am) as those individuals implementing the UV protocol treatment.

TABLE 2

Static Validation of the 30 min UV Radiation Protocol in a Typical Family Room

| CKs: min after a point, no UV protocol* (min) | Capturing time (min) | colony counting (colony/plate) | | | | | | | | |
|---|---|---|---|---|---|---|---|---|---|---|
| | | 0 | Avg | SD | 2 m | Avg | SD | 3 m | Avg | SD |
| 20 | 5 | 17, 15, 22, 13, 20 | 17.4 | 3.65 | 15, 21, 17, 16, 20 | 17.8 | 2.59 | 19, 15, 15, 13, 14 | 15.2 | 2.28 |
| | 15 | 20, 21, 18, 22, 19 | 20.0 | 1.58 | 25, 23, 18, 22, 19 | 21.4 | 2.88 | 21, 26, 18, 22, 19 | 21.2 | 3.11 |
| 40 | 5 | 15, 14, 13, 19, 21 | 16.4 | 3.44 | 16, 15, 18, 23, 20 | 18.4 | 3.21 | 17, 15, 20, 18, 20 | 18.0 | 2.12 |
| | 15 | 18, 21, 18, 22, 15 | 18.8 | 2.77 | 20, 21, 18, 22, 24 | 21.2 | 2.59 | 24, 25, 18, 22, 19 | 21.6 | 3.05 |
| 60 | 5 | 18, 18, 19, 14, 21 | 18.0 | 2.55 | 22, 15, 14, 19, 20 | 18.0 | 3.39 | 16, 18, 22, 26, 20 | 20.4 | 3.85 |
| | 15 | 16, 20, 25, 22, 21 | 20.8 | 3.27 | 28, 20, 18, 16, 19 | 20.2 | 4.60 | 22, 26, 18, 22, 21 | 21.8 | 2.86 |

| Treatments: mm after UV protocol endpoint (min) | capturing time (min) | 0 | Avg | SD | 2 m | Avg | SD | 3 m | Avg | SD |
|---|---|---|---|---|---|---|---|---|---|---|
| 20 | 5 | 3, 0, 0, 4, 0 | 1.4 | 1.95 | 0, 0, 5, 1, 3 | 1.8 | 2.17 | 4, 0, 3, 0, 0 | 1.4 | 1.95 |
| | 15 | 0, 5, 4, 0, 2 | 2.2 | 2.28 | 4, 8, 0, 4, 0 | 3.2 | 3.35 | 2, 0, 0, 1, 0 | 0.6 | 0.89 |
| 40 | 5 | 0, 0, 1, 1, 7 | 1.8 | 2.95 | 3, 5, 0, 2, 1 | 2.2 | 1.92 | 1, 1, 7, 0, 3 | 2.4 | 2.79 |
| | 15 | 0, 2, 5, 6, 9 | 4.4 | 3.51 | 8, 6, 7, 11, 0 | 6.4 | 4.04 | 3, 2, 7, 9, 0 | 4.2 | 3.70 |
| 60 | 5 | 1, 1, 3, 0, 4 | 1.8 | 1.64 | 5, 1, 0, 6, 0 | 2.4 | 2.88 | 7, 3, 0, 5, 8 | 4.6 | 3.21 |
| | 15 | 2, 4, 0, 3, 5 | 2.8 | 1.92 | 7, 6, 0, 5, 0 | 3.6 | 3.36 | 3, 9, 3, 4, 0 | 3.8 | 3.27 |

***The room hasn't used any UV quarantine system for a week, choose the same clock time point with the contrast experiment (with the 30 min UV protocol).

In Table 2 where there are treatments at 20, 40, and 60 minutes after the UV (disinfection) protocol endpoint in comparison to CKs, the viable colony counting is performed at distances of 0 meters, 2 meters, and 3 meters from the center. The implementation of the UV (disinfection) protocol leads to colony counts which are 10-fold less than the colony counts for CKs. This means that 30 minutes of UV disinfection, as described above, in a static ordinary room (i.e., the enclosed area) significantly kills most of the airborne pathogens and microbes. The UV lamps used during UV disinfection can kill 99% of surface bacteria within seconds. Laboratory and industrial cleanroom procedures are also disinfected by the UV lamps for 30 minutes. The survival rate of the RNA coronaviruses is lower than bacteria and eradicated faster than the surface bacteria.

Example 6—Dynamic Spraying Simulation

Figure 9:
FIG. 9 is a depiction of agar capturing, spraying, and illumination, in accordance with the principles of the invention.

A commercial spray bottle is selected by checking if it can spray DH5a exponential stage LB broth into visually fine droplets. DH5a exponential stage LB broth suspension from 250 milliliter (mL) flasks on a rotary shaker is: (i) passed through an ordinary chemical filter paper first; (ii) adjusted by a Petroff-Hausser chamber to $10^6$ cell/mL; and (iii) sprayed, as depicted in FIG. 9. Each spray releases a 0.7-1.5 mL suspension. As depicted in the center image of FIG. 9, the length of liquid mark on the wall, as obtained by this spraying bottle, is less than 40 cm. The distance of the visual smog made by this bottle can only reach around 60 cm. This 60 cm distance is the maximum distance in which most large droplets from the spraying bottle can reach. By virtue of the poor visibility or absence of visibility of small-sized aerosol and droplet particles in the airflow, it is difficult to determinate the speed and distance the small-sized aerosol and droplet particles in the airflow. Indirect methods are therefore used to simulate the distance and speed of small-sized aerosol and droplet particles in the airflow.

As with the static validation for room and sampling point designs, 30 min after the time endpoint of the UV protocol is implemented. Three treatments, as listed in Table 3, include capturing without DH5a spraying, capturing with sprays not passing a UV box, and capturing with sprays passing by a UV box on the same colony counting method in static room. A spray bottle is applied 20 cm above the top of the UV radiation box with a 30 W UV lamp shinning inside, while spraying horizontally to each sampling point, as depicted in the right image of FIG. 9. After implementing 30 min UV protocol and another 30 minutes, one horizontal spray is applied from the center to each sampling point. After 5 minutes, plates at the same height are sprayed; captured for 5 minutes; and sealed for incubating.

TABLE 3

Dynamic Spraying Validation of 30 min during UV Protocol for Moving Airborne Infectious Agents

|  | colony/plate at 2 min | | | colony/plate at 3 m | | |
|---|---|---|---|---|---|---|
| Capturing without DH5α spraying | 5, 3, 1, 0, 1 | 2.0 Avg | 2.00 SD | 2, 0, 3, 2, 0 | 1.4 Avg | 1.34 SD |
| Capturing with sprays not passing a UV box | 24, 21, 20, 17, 23 | 21.0 Avg | 2.74 SD | 22, 19, 22, 18, 16 | 19.4 Avg | 2.61 SD |
| Capturing with sprays passing by a UV box | 7, 9, 5, 0, 10 | 6.2 Avg | 3.96 SD | 8, 11, 7, 5, 1 | 6.4 Avg | 3.71 SD |

The results in Table 3 at 2 minutes and 3 minutes after 30 minutes implementing the UV protocol are similar to the corresponding results in Table 2. Spraying treatment increases the average viable capturing colony from 2.0 at 2 minutes and 1.4 at 3 minutes to 21.0 at 2 minutes and 19.4 at 3 minutes, respectively, when capturing without DH5a spraying and capturing with sprays not passing a UV box. The liquid mark or smog produced by the spraying bottle can be visually achieved at distances less than 60 cm, where the spray contacts the air, which may contain airborne pathogens. At the sampling point at 2 minutes and 3 minutes, only 5 minutes of traveling time is allowed. Colony counting significantly increased around to 10-fold. This is due to the attainment of invisible small-sized aerosol & droplet particles, which ae similar to those described from other literature.

For sprays over the UV radiation box at 2 minutes and 3 minutes, average colony counting is reduced from 21, 19.4 to 6.2, 6.4 respectively. This means UV radiation can kill the airborne microbes in the small-sized aerosol particles of moving airflow. It is difficult to determine the exact speed of these small-sized aerosol particles due to rapid movement of droplets. Our simulation can show that: (i) these small-sized aerosol or droplet infectious particles do travel to viable there with a higher impact and (ii) UV radiation can significantly kill these moving infectious agents inside airflow under the experimental conditions. These experiments are performed for indoor space. For outdoor environments, windless public regions can exhibit similar results. Under breeze outdoor condition, the wind parameters add to the complexity for UV disinfection protocol. Airflow can drive off aerosol coronavirus in an enclosed region and carry viruses to infect remote people under certain conditions. Therefore, it is not plausible that the social distancing rule is safer for outdoor public regions than for indoor public regions. However, this result is enough to suggest the upgrading of the "social distancing" rule into the "Airflow Inaccessible Distancing" protocols. Also, this validation shows the UV radiation box (wall) is significantly effective. In our real application, UV radiation box may be more acceptable than that of UV hood even if there are instances of the UV radiation box being less effective than the UV hood. The UV radiation box can be used in less infected regions as compensation for UV hood method.

Example 7—Validation of UV Ultimate Method or UV Hood Method

Within the enclosed area, a UV lamp is continuously switched on.

Individuals within the enclosed area use UV hoods, on which safety is tested by a high-resolution UV meter. Spray bottles, as used in Example 6, are applied in combination with activated UV lamps in an enclosed area. UV hood protections, which have been validated as effective in guarding against UV exposure by a UV meter with a resolution of 0.1 0.1 μw/cm², are in use by individual(s) in the enclosed area. In the center of the enclosed area, the spray bottle is applied spray 5 times with 1-second interval to each sampling point. After 5 min of spraying, agar plates are opened for 5 min, thereby capture for each point at 0 minutes, 2 minutes, and 3 minutes, similarly as above. The 0-minute sampling point represents the spray bottle location. Approximately 10 seconds after finishing spraying each sample point, directly open five (5) agar plates and expose for 30 seconds. The colony counting is obtained as indicated in Table 4.

TABLE 4

DH5α Spray Viable Colony Counting for Aerosol
Travel Distance at 2 Minutes and 3 Minutes where the Designed UV
Lamps are Switched on, to Verify the UV Ultimate Method

| Minutes after UV lamp is turned on | colony/plate | | |
|---|---|---|---|
| | 0 min. | 2 min | 3 min |
| 0 | 0, 0, 0, 0, 0 | 0, 0, 0, 0, 0 | 0, 0, 0, 0, 0 |
| 20 | 0, 0, 0, 0, 0 | 0, 0, 0, 0, 0 | 0, 0, 0, 0, 0 |
| 40 | 0, 0, 0, 0, 0 | 0, 0, 0, 0, 0 | 0, 0, 0, 0, 0 |
| 60 | 0, 0, 0, 0, 0 | 0, 0, 0, 0, 0 | 0, 0, 0, 0, 0 |

The result demonstrates that UV hood or UV ultimate quarantine methods can 100% stop the infectious agent in the airflow, while the UV lamp is switched on. Under these experimental conditions, the traveling distance of even the most challenging small-sized aerosol particles is 0-meter. The only difference between the 30-minute UV protocol and the UV ultimate method is whether people can go on-site while the UV lamp is switching on. The 30-minute UV protocol only operates while no person is on-site. Therefore, the 30-minute UV protocol still offers some traveling opportunities for viral aerosols. Also, the 30-minute UV protocol is not as effective as the UV-ultimate method in preventing the infectious agents from individuals after the UV radiation is switched off. The UV ultimate method where individuals put on (i.e., wear, thereby using) the UV hood within the enclosed area reduces travel time of viral aerosol to 0 seconds. Therefore, the UV ultimate method provides complete effectiveness in killing infectious agents under almost all conditions similar to public use regions. This shifts the safety of UV protection from the infectious agent.

Example 8—Safety of Self-Made UV Hoods or Alternates to UV Hoods

The efficacy of the UV hoods in providing suitable protection can be assessed by portable UV meters. An individual is wearing a UV hood, and thereby shielded by a UV hood. A sensor may be attached to a sidewall in an enclosed area which faces the individual wearing the UV hood. The entirety of the UV protecting area of the UV hood (i.e., covering of areas of skin that are at risk for UV exposure) is assessed. If the radiation is below the safety threshold, then the radiation is safe to apply in the enclosed area.

The expected physical life of UV lamps is generally 8,000-16,000 operating hours when the lamp is switched on once per day. The actual physical life of UV lamps tends be less due to the frequent operating. Germicidal UV lamps generally define the UVC 253.7 nm radiation decay to 70% as the standard for the end of the functional life time, as measured in hours. The UV radiation strength is inversely proportional to the square of the distance parameter to the emission source. Thus, UV lamps are generally installed at less than 2.5 meters height for measuring the strength decay, where there is a 1-meter perpendicular distance from the UV lamp. Stated another way, a portable variant of the UV meter measures the radiation performance curve or functional life of a UV lamp to determine a resolution value or span. For example, the UV lamp in the systems and methods herein has a resolution span of 39.99 $\mu W/cm^2$ to 39.99 $mW/cm^2$. In other examples, high-resolution product UV meters have a resolution of 0.1 $\mu W/cm^2$. In alternate examples, a portable Geiger counter, which can be place below the slits, are used to determine a resolution value or span. In other alternate examples, the Geiger counter are oversensitive and generally detect environmental radiation background. The Geiger counters measure beta radiation ((3), gamma radiation (y), and part of x-rays from the surrounding environment. The UV lamps are switched off to obtain the environmental read. The UV lamps are subsequently switched on after shielding to determine if there any shifts in the environmental read. Any shift in the environmental read lower than 10% is deemed to be safe.

Example 9—Implementation of the "Airflow Inaccessible Distancing" Protocols Via Plastic Films Mask designs do not prevent the infection as the airflow still contains contagious agents. The infection UV quarantine device actively kills the contagious agents in the airflow. When the airflow shuts down in, for example, an ordinary 14 $m^2$-retail store, airborne contagious agents are effectively quarantined. This is a highly effective physical airflow quarantine for preventing the infection. The three employees in the 14 $m^2$-retail store do not use masks since there is a UV radiation box inside the store. The coronavirus is carried by the airflow to be spread infection. The air exchange size of the 14-$m^2$-retail store is restricted to a small hole, thereby decreasing the chance of airborne virus infecting individuals. Other individuals can visit the 14 $m^2$-retail store to purchase items at the plastic film covering windows and the hole located at elbow height. This arrangement of the plastic film and location of the hole reduces the effectiveness of the aerosol virus infecting individuals. The plastic film is typically transparent and disinfected on both sides with UV radiation. The plastic film is used in combination with: (i) a 30-minute UV radiation protocol before entering the store; and (ii) a UV radiation box, which is lit up, for healthy employee.

Example 10—E. coli Verification of Airflow Inaccessible Distancing

E. coli spraying can verify the efficacy of the process in Example 9. In the spray experiment, a simple plastic film, which can stop airflow, also effectively stops any sprays from penetrating through the film. The "airflow inaccessible distancing" is reduced to zero beyond the plastic film. E. coli sprays cannot invade into the room unless directly sprayed from the hole and inside the store. Ventilation is on the roof, which is safe for in-store people to get breath air.) This simple plastic film, combined with the UV radiation box, is much more effective to prevent the COVID-19 infection than the conventional quarantine system.

Example 11—The Infection UV Quarantine Device in a Passenger Car

A passenger car uses a plastic film system to separate the drivers from passengers, in combination with the infection UV quarantine device. The effectiveness of the plastic film system is still based on the "airflow inaccessible" principle. The average human respiratory rate is 30-60 breaths per minute at birth and decreases to 12-20 breaths per minute in adults. An estimation of the residual volume is 18.1 ml/kg for infants or a proportion of vital capacity for adults is 0.24 for men and 0.28 for women. The "airflow inaccessible distancing" can be modified to conform to the individuals within the enclosed area as to not completely obstruct the flow of air.

Example 12—Preparation of DH5α Suspension

DH5α suspension is prepared from the secondary inoculation exponential growth stage culture with LB broth in a 250 mL sterilized flask on a 37±1° C. rotary shaker. LB agar plates, the spray bottle, and quartz glass UV disinfection lamps are used in unison. More specifically, an 8 Watt-UV lamp provides effective disinfection for a 12 m² static indoor space, as validated by SGS. Portable UVC light meters and the Geiger-Müller counters measure radiation levels. Plastic films transmit UV radiation and do not change transparency.

Example 13—Preparation of Agar Plates

After collecting particles on agar plates, each agar plate is sealed with a parafilm, incubated at 37° C. for 24 hours, analyzed for colony growth, and stored with the original seal in a refrigerator (0-4° C.). While in use, the temperatures of sealed plates are balanced. The spraying bottle with 106 DH5α suspension leaves liquid marks on the wall. The length of this mark is less than 40 cm. The distance of the visual spraying smog made by this spraying bottle can only reach around 60 cm. This 60 cm distance should be the maximum distance in which most large droplets from the spraying bottle can reach. The spraying bottle with a tip is 20 cm above a UV radiation box loaded with DH5α suspension from the spray bottle. Stated another way, the 106 DH5α suspension is sprayed over the UV radiation inside the box against a dark background, thereby appearing as a shining reflection. The sprayed suspension only reaches a small range, while invisible small-sized aerosol particles can reach up to 3 meters. This UV radiation box is made from a cardboard box with the following dimensions: 33×44×54 cm and a thickness of 4.5 mm. A commercial UV meter with a resolution of 0.1 μw/m² does not detect any UV leaking wen directly attaching the sensor on the whole outside wall of the UV radiation box and the 60-watt UV lamps inside the UV radiation box emit radiation. In other experiments, 30-watt UV lamps, explosion resistant safety glasses, and remote-controlled UV-lamps are used.

Example 14—Comparison of Infection UV Quarantine and Convention Quarantine in a Public Area Within an enclosed area that is 2×2 m² public area, there is a single health individual and a single infected individual go in and out of the public area every minute over an 8-hour period every day. If the healthy individuals use masks and protective clothes to prevent infection, then some of the high impact masks or protective equipment need to resist 8×60=480 infected people's aerosol and other touched surfaces. Touched surfaces may be not be sanitated properly, which increases the likelihood of spreading injection. Masks are useless when individuals are too close to each other, even if the masks are disposable. Protective clothes are generally not disposable. However, the daily cleaning and changing of these protective clothes need complex equipment and protocols that are generally challenging for untrained individuals. Therefore, long term use of protective clothing is also a risk. The application of chemical sanitizers in the enclosed area is also challenging. Theoretically, each infected individual goes in and out, such that the enclosed area needs 480 rounds of sanitation. Rounds of sanitation lower than 480 correspond to increased risk of spreading contagious agents. Also, chemical sanitation only deals with contaminated surfaces, which is insufficient for aerosol contaminants in the air. In contrast, emission of UV light in the 2λ2 m² public area region for 8 hours is enough to prevent all the infection under the same conditions. This is also cost-effective as the individuals use some sort UV protection (e.g., UV hood or UV radiation box) when moving in and out of the 2×2 m² public area region for 8 hours. UV protection, which costs less than quarantine clothes, is easy for people of varying skill in the art to implement. Thereby, the UV radiation and UV protection are effective at stopping the infection.

The UV radiation and UV protection are able to achieve 100% efficacy in stopping the spread of the injection, even under severe infection emergency conditions. UV radiation with personal protection can effectively replace routine precautions such as masks, protective clothes, chemical sanitation, quarantine hospitals, etc., under severe infection emergency conditions.

Example 15—Infection UV Quarantine Device Applied in an Office Setting

A UV lamp with remote control resides at an office table. The remote control has 15 seconds of lag time with beeps, which helps individuals to avoid directly becoming exposed to UV radiation. Before entering into the office room, the UV lamp is turned on and allowed to irradiate the office room for 30 minutes (i.e., UV disinfection). After 30 minutes of UV disinfection for the table, the table can be used. A cardboard box is used to construct the UV radiation box. The UV lamp inside the UV radiation box can continuously produces ozone to kill Coronavirus. The ozone can cause damage to the skin or eyes so it is advisable not to stare at the UV lamp when switched on. A used face mask can be decontaminated by exposure from the UV lamp for 30 minutes, and thus suitable for reuse. The UV lamp is continuously shining inside the UV radiation box, while no UV radiation and Ozone directly impinge exposed skin. The ozone produced by the UV lamp permeates the room to kill the coronavirus.

Example 16—Smaller UV Radiation Wall Box

A smaller UV radiation wall box can be used when two individuals speak to each other when facing each other, as described above. The small UV radiation box, which is composed of a cardboard box, is placed between the two individuals speaking to each other, wherein the individuals do not need to wear masks to control the spread of airborne pathogens when doing so. Masks do not filter viruses and can only reduce the concentration of aerosol virus invading into the sacrificed human respiratory system. Suppose in a certain enclosed area, one deep breath inhales X concentration of aerosol coronavirus without a mask. Under the same condition, inhaled coronavirus concentration with masks can be reduced to around 0.3-0.6λ. Masks can only reduce the concentration of inhaled viruses and can never eliminate them. Tt is still dangerous for individuals with masks to close to each other. While two individuals approach a closer distance to each other, masks become useless for protecting them from infection. For this reason, a UV radiation box is more effective than masks in the enclosed area. As mentioned, masks can only reduce the inhaled virus concentration to 0.3-0.6λ, whereas the UV radiation box under the same condition can easily reduce the inhaled virus concentration below 0.001λ. While using the UV radiation box, there is a slight ozone smell in the air. The radiation emitted within the UV radiation wall does not directly shine on exposed human skin. The virus killing efficiency of the UV radiation wall is even higher than that of the UV radiation box. A multi-space washroom is another enclosed area that can achieve disinfection via a UV radiation box placed in each space. Washrooms are areas that facilitate the spread of contagious agents. Thus, disinfection of washrooms is effectively halting the spread of airborne pathogens and microbes.

Example 17—The Infection UV Quarantine Device in Private Family Rooms

At the family entrance door (outside), UV lamp emits radiation to clean the outside entrance door. Just after every member of the family returns back to the home, 30-minute irradiation is implemented, as described in the UV protocol. This prevents the accumulation of coronavirus in the irradiated region. At the family entrance corridor (inside), outside shoes and clothes are exposed to 30-minute UV disinfection. For houses without such a corridor, the UV lamp can be used in the same way. UV lamps in the basement, near the ventilation air inlet, there are eight UV lamps of different sizes. The calculation of the numbers of UV lamps in this region is based on the product instruction that an 8 W UV disinfection lamp can cover 12 m² static area. Due to the air from the air-condition ventilation being sent to all rooms within the house, the number of UV lamps should be enough to cover the total area of all rooms of the house and not just the basement. Such an air inlet UV control method is relatively simple, as there is no need to take care of every air outlet in each room. The basement UV lamps are used with a curtain which at least partially covers the UV lamp. This prevent the UV radiation from directly shining on the individual walking around and preventing access to this region. If there is a lack of control of the ventilation air inlet by UV lamps, then every ventilation outlet is equipped with a UV lamp and a cardboard box (i.e., the UV radiation box) to shield the UV lamp from hurting individuals walking around. In an apartment or condo, control of the ventilation system is critical as the rooms share a central air condition. Therefore, in an apartment or condo, it is critical to use UV lamps at each ventilation outlets in combination with UV shielding, such as a UV radiation box. Ventilation control by UV quarantine should be implemented 24 hours per day/7 days per week when air inlet control conditions are not well established. These protocols can be implemented, for example, on these other enclosed areas: family gyms, family study tables, family shower and washroom, family kitchen and diner table, family pianos, kid rooms, the bed in the bedroom, and family cars. A virus infection is triggered (i.e., sufficient viral load for causing illness) at a certain concentration threshold. If a person goes to work every day and always contacts with the virus at a lower than infection threshold, the virus concentration possibly accumulates inside the car to attain the threshold over an extended period and cause illness. UV disinfection of the systems and methods herein can stop the virus accumulation process in enclosed areas.

The UV protocol of 30-minute UV disinfection plus enough shielded UV radiation boxes when emitting ozone can greatly inhibit the coronavirus infection. Especially for a quarantine hospital, the ventilation system can be controlled by the combination of the UV lamp and UV radiation boxes. However, for public regions with more individuals coming in and out at a higher frequency, such as customs, airplanes, cinema, large slaughtering houses, etc., or for severely infected districts even without such frequent visits, the ultimate UV quarantine method is implemented.

Example 18—Ultimate UV Quarantine Method with UV Hood in UV Lamp Active Public Regions Goggles and umbrellas can be used for UV quarantines in UV Lamp Active Public Regions. In a community of 80% infection, the ultimate UV quarantine method with UV hoods protect the remaining 20% free from the infection. When implementing the UV quarantine method, the infection rate is 80% despite the infected cohort and non-infected cohort interacting. Thereby, the UV hood and UV lamp of the ultimate UV quarantine method are effectively halting the spread of COVID-19 or other biological infectious agents.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated. In addition, when a single callout line in the drawings leads to two or more separate reference numbers (first, second, etc. reference numbers), (and each reference numeral refers to a different piece of text in the detailed description) and it would be inconsistent to designate the drawing item being called out as both pieces of text, the drawing be interpreted as illustrating two different variants. In one variant, the drawing item is referred to by the first reference number and in another variant the drawing item is referred to by the second reference number, etc.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether CTRL logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for ultraviolet (UV) disinfection, comprising:
   irradiating with UV light within an enclosed area with an infection UV quarantine device;
   shielding individuals within the enclosed area with UV shielding technology, wherein the UV shielding technology comprises a UV hood for shielding a head, the UV hood comprising a mouth piece, a lamp mount for receiving a UV lamp emitting the UV light, an interface connecting the mouth piece to the lamp mount, a respiratory box with vent holes and tubes within the mouth piece and interface for conducting air irradiated by the UV light to the mouth piece and into the hood, the tubes being configured to conduct the irradiate air into the hood while preventing UV leakage into the hood;
   reducing accessibility of airborne pathogens and respiratory droplets within the enclosed area to individuals by killing airborne pathogens and respiratory droplets within the enclosed area;
   measuring UV exposure levels of the individuals within the enclosed area by utilizing a UV meter; and
   wherein the infection UV quarantine device comprises the UV lamp.

2. The method of claim 1, wherein the UV lamp emits 240-280 nanometer radiation, wherein the radiation is germicidal to airborne pathogens and the respiratory droplets.

3. The method of claim 1, wherein the airborne pathogens are selected from the group consisting of: COVID-19, Newcastle disease, measles, morbillivirus, chickenpox, *Mycobacterium tuberculosis*, influenza, enterovirus, and norovirus.

4. The method of claim 1, wherein the respiratory droplets range from 5 micrometers and 1000 micrometers.

5. The method of claim 2, wherein 240-280 nanometer radiation travels up to 15 meters from the UV lamp.

6. The method of claim 1, wherein shielding the individuals within the enclosed area with UV shielding technology comprises covering skin of the individuals within the enclosed area.

7. The method of claim 2, wherein the UV lamp emits 240-280 nanometer radiation for 30 minutes.

8. A method for ultraviolet (UV) disinfection, comprising:
   irradiating with UV light within an enclosed area with an infection UV quarantine device;
   shielding individuals within the enclosed area with UV shielding technology, wherein the UV shielding technology comprises a UV hood for shielding a head, the UV hood comprising a mouth piece, a lamp mount for receiving a UV lamp emitting the UV light, an interface connecting the mouth piece to the lamp mount, a respiratory box with vent holes and tubes within the mouth piece and interface for conducting air irradiated by the UV light to the mouth piece and into the hood, the tubes being configured to conduct the irradiate air into the hood while preventing UV leakage into the hood;
   reducing accessibility of airborne pathogens and respiratory droplets within the enclosed area to individuals by killing airborne pathogens and respiratory droplets within the enclosed area;
   measuring UV exposure levels of the individuals within the enclosed area by utilizing a UV meter; and
   wherein the infection UV quarantine device comprises a UV lamp;
   wherein the UV lamp emits 240-280 nanometer radiation, wherein the radiation is germicidal to airborne pathogens and the respiratory droplets and traveling up to 15 meters from the UV lamp for 30 minutes;
   wherein the airborne pathogens are selected from the group consisting of: COVID-19, Newcastle disease, measles, morbillivirus, chickenpox, *Mycobacterium tuberculosis*, influenza, enterovirus, and norovirus;
   wherein the respiratory droplets range from 5 micrometers and 1000 micrometers;
   wherein shielding the individuals within the enclosed area with UV shielding technology comprises covering skin of the individuals within the enclosed area.

* * * * *